United States Patent
Matsuura et al.

[11] Patent Number: 5,113,680
[45] Date of Patent: May 19, 1992

[54] APPARATUS FOR DETECTING INTENSITY AND/OR DENSITY OF SHOT BLASTING

[75] Inventors: Makoto Matsuura; Hironobu Amano; Kunio Ohta, all of Toyokawa, Japan

[73] Assignee: Sintokogio Ltd., Nagoya, Japan

[21] Appl. No.: 696,888

[22] Filed: May 8, 1991

[30] Foreign Application Priority Data

May 10, 1990 [JP] Japan .................................. 2-120507

[51] Int. Cl.⁵ ............................ B24C 1/10; G01L 5/00
[52] U.S. Cl. ............................................. 72/53; 73/11; 73/861.73
[58] Field of Search ................... 72/53; 81/319, 320; 73/11, 658, 661, 861.73, 862.53, 12

[56] References Cited

U.S. PATENT DOCUMENTS

| | | | |
|---|---|---|---|
| 3,640,135 | 2/1972 | Tomiyasu et al. | 73/861.73 |
| 4,354,622 | 10/1982 | Wood | 73/861.73 |
| 4,441,101 | 4/1984 | Robar | 73/861.73 |
| 4,470,292 | 9/1984 | De Clark et al. | 73/11 |
| 4,805,429 | 2/1989 | Thompson | 72/53 |
| 4,848,123 | 7/1989 | Thompson | 72/53 |

FOREIGN PATENT DOCUMENTS

| | | | |
|---|---|---|---|
| 168890 | 1/1986 | European Pat. Off. | 73/861.73 |
| 2403227 | 8/1974 | Fed. Rep. of Germany . | |
| 272247 | 10/1989 | Fed. Rep. of Germany . | |

OTHER PUBLICATIONS

"Shot Peening Ductile Iron", Modern Casting Feb. 1990, pp. 51-53.

Primary Examiner—David Jones
Attorney, Agent, or Firm—Armstrong, Nikaido, Marmelstein, Kubovcik & Murray

[57] ABSTRACT

Disclosed is an apparatus for detecting at least one of an intensity and a density of shot blasting during shot treatment, which includes a shot bombardment and propagation member including a first part to be bombarded by a shot stream for generating elastic waves when bombarded by the shot stream and a second part for propagating the elastic waves therethrough, a transducer for receiving the elastic waves from the shot bombardment and propagation member and transducing the elastic waves into a high-frequency electrical signal, and a measuring circuit detecting at least one of the number of times of shot bombardment and the intensity of shot bombardment on the basis of the high-frequency electrical signal.

15 Claims, 4 Drawing Sheets

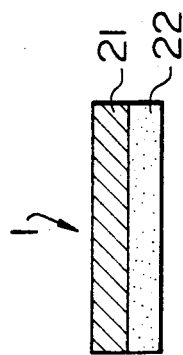
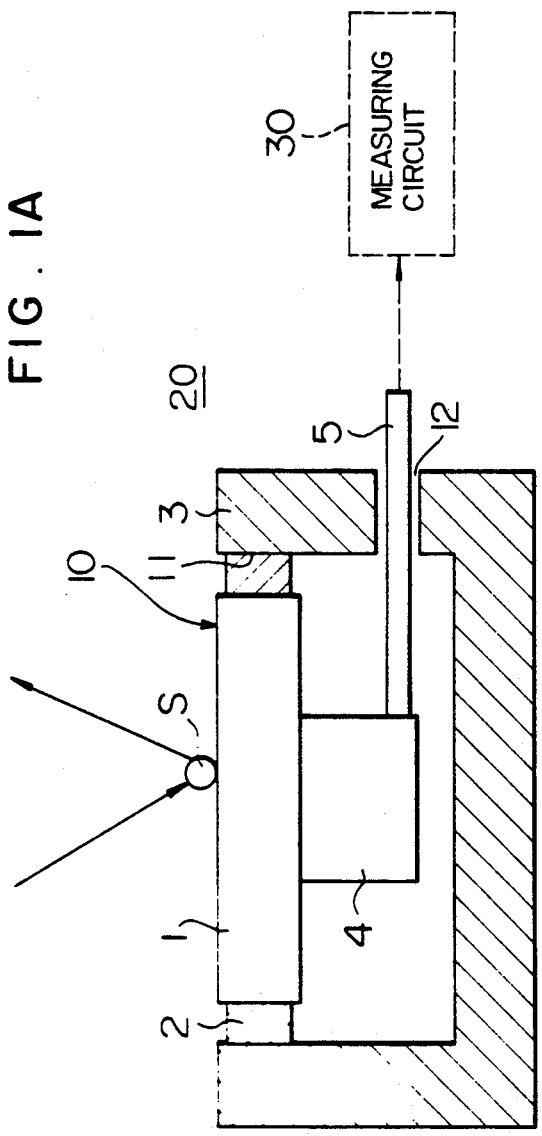
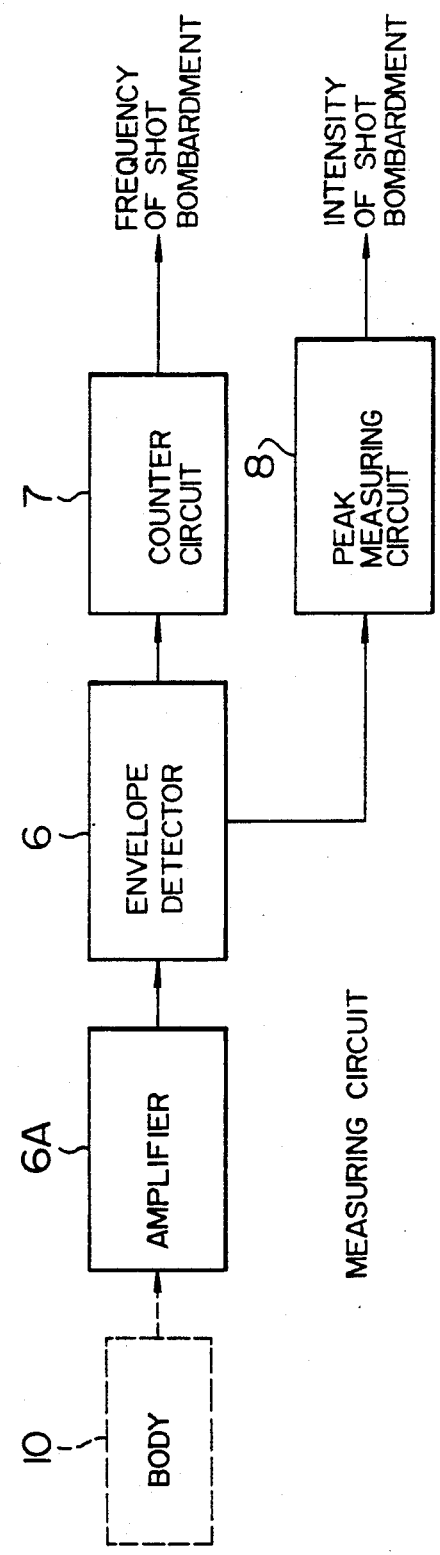

HIGH-FREQUENCY ELECTRICAL SIGNAL

ENVEROPE DETECTION

APPARATUS FOR DETECTING INTENSITY AND/OR DENSITY OF SHOT BLASTING

BACKGROUND OF THE INVENTION

1. Field of the Invention

This invention relates to an apparatus for detecting the intensity and/or the density of shot blasting used for shot treatment, and more particularly to an apparatus which can detect the intensity of shot blasting while a work is being subjected to shot treatment.

2. Description of the Related Art

In shot treatment, such as, so-called shot blasting or shot peening, a shot stream of beads of a hard material, such as, steel, aluminium, zinc, glass or ceramics, having a diameter of about 0.2 to 2.0 mm is projected toward and onto the surface of a steel work so as to remove scale or burr from the surface of the steel or aluminium work or so as to harden the surface of the steel or aluminium work. Hitherto, the average intensity or the density of such a shot stream is measured for detecting the intensity of the shot blasting or shot peening, as described in, for exmaple, "Shot Peening Ductile Iron", Modern Casting/February 1990, pp. 51-53. That is, utilizing the fact that, when a steel strip is subjected to projection of a shot stream, the steel strip tends to deflect or bend upward toward the side that has received the shot, this arc height in deflection is measured by a gauge so as to detect the average intensity of the shot stream. Also, the dimpling formed on the surface of the steel strip by projection of the shot stream is photographed, and the rate or coverage of the dimpling is then measured so as to detect the density of the shot stream. However, in these methods for detecting the degree of shot blasting or shot peening, the steel strip is subjected to the measurement by taking out the steel strip from a shot blasting machine after completion of the shot blasting treatment. Thus, although these methods are preferable for determining beforehand the conditions of shot blasting, it is difficult to utilize these methods for carrying out shot blasting under optimum conditions while monitoring the actual intensity and/or density of the shock stream.

SUMMARY OF THE INVENTION

With a view to solve the prior art problem described above, it is an object of the present inventtion to provide an apparatus which can detect the intensity of a shot stream and/or the density of the shot stream during shot blasting.

An embodiment of an apparatus for detecting the intensity and/or density of the shot blasting according to the present invention which attains the above object comprises: shot bombardment and propagation means including a first part to be bombarded by a shot stream thereby generating elastic waves and a second part for propagating the elastic waves generated from the first part; transducer means connected to the second part for receiving the elastic waves propagated through the second part and transducing the received elastic waves into a high-frequency electrical signal; and measuring means including a counter circuit connected to the transducer means for detecting single-waves contained in the high-frequency signal, each single-wave corresponding to one shot and having a wave form whose amplitude increases larger than a predetermined threshold and then reduces to less than the threshold, and counting a number of the detected single-waves, and a peak measuring circuit for detecting a peak value of each of the detected single-waves.

BRIEF DESCRIPTION OF THE DRAWINGS

FIG. 1A is a schematic sectional view showing the arrangement of components forming an embodiment of the apparatus for detecting the intensity and/or the density of shot blasting or shot stream according to the present invention.

FIG. 1B shows the structure of one form of the shot bombardment and propagation member in the embodiment shown in FIG. 1A.

FIG. 2 is a block diagram showing the structure of the measuring circuit in the embodiment shown in FIG. 1A.

DESCRIPTION OF THE PREFERRED EMBODIMENTS

Figure 3:
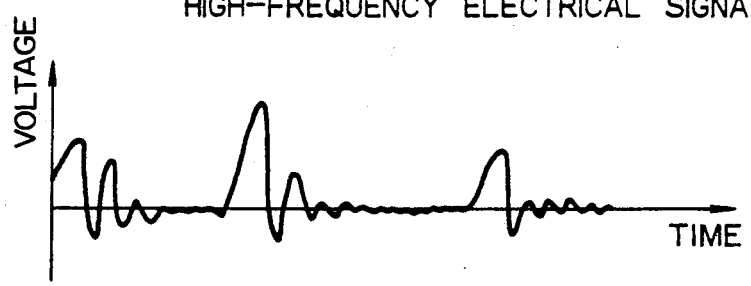
FIG. 3 shows the waveform of a high-frequency electrical signal obtained by transducing elastic waves generated from the first part when this part is bombarded by a shot stream.

Preferred embodiments of the present invention will now be described in detail by reference to the accompanying drawings.

FIG. 1A is a schematic sectional view showing the arrangement of components forming an embodiment of the apparatus 20 according to the present invention. Referring to FIG. 1A, a circular shot bombardment and propagation member 1 acts as both the first part to be bombarded by a shot stream for generating an elastic wave when bombarded by shot S and the second part for propagating the elastic wave. The shot bombardment and propagation member 1 is fixed to an outer casing 3 through an annular vibration isolating member 2. The member 2 is preferably composed of rubber. More concretely, this member 1 is in the form of a circular plate which is made of a wear resistant material such as carburized steel, sintered hard alloy or ceramics, which has, for example, a diameter of 20 mm and a thickness of 10 mm, and the both surfaces of which are polished. As shown in FIG. 1B, this member 1 may be in the form of a composite in which the first part 21 made of carburized steel, sintered hard alloy or ceramics and the second part 22 made of cast iron, aluminium, steel or phenolic resin are bonded together. This member 1 may have a diameter of 5 to 30 mm and a thickness of 3 to 30 mm.

The outer casing 3 is in the form of a box having a generally square upper wall and a generally square bottom wall. The outer casing 3 is formed in its upper wall with a circular opening 11 in which the member 1 is mounted through the annular vibration isolating rubber 2. Also, the outer casing 3 is formed in one of its side walls with a hole 12 through which a cable 5 extends to the outside. A transducer (for example, an acoustic emission sensor or AE sensor) 4 is mounted on the lower surface of the member 1 for receiving propagated elastic waves and transducing the waves into a high-frequency electrical signal.

The cable 5 extending through the side wall of the outer casing 3 is connected at one end to the transducer 4 and at the other end to a measuring circuit 30.

FIG. 2 shows the structure of the measuring circuit 30. Referring to FIG. 2, an envelope detection circuit 6 is connected through an amplifier circuit 6A to the other end of the cable 5 for detecting envelope of the high-frequency electrical signal. A counter circuit 7 counting the number of single-waves contained in the output signal generated from the envelope detection circuit 6 and a peak measuring circuit 8 measuring the peak values of the single-waves generated from the envelope detection circuit 6 are connected to the envelope detection circuit 6.

Figure 4:
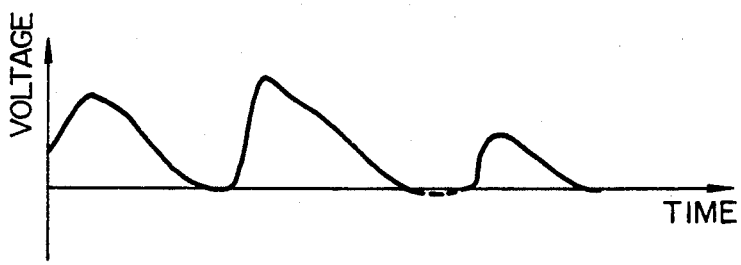
FIG. 4 shows the waveform of a detection output signal obtained as a result of envelope detection for the high-frequency electrical signal.

The high-frequency electrical signal generated from the transducer 4 and applied through the amplifier circuit 6A to the envelope detection circuit 6 has a voltage waveform as shown in FIG. 3. In the case of the waveform shown in FIG. 3, the high-frequency electrical signal includes three single-waves. When this high-frequency electrical signal is supplied to the envelope detection in the envelope detection circuit 6, the circuit 6 generates a detection output signal having a voltage waveform as shown in FIG. 4.

Figure 5:
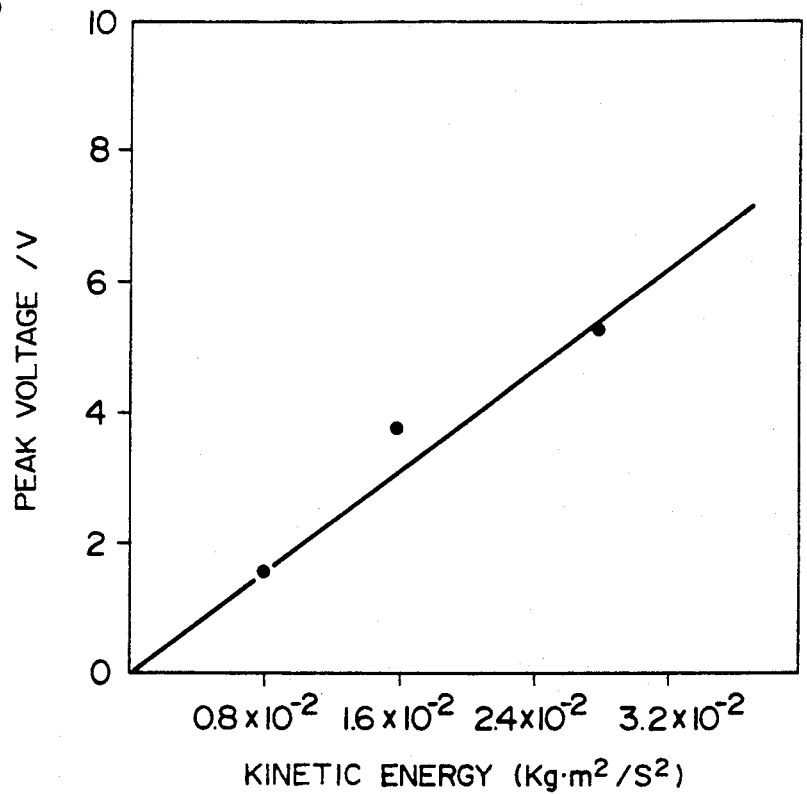
FIG. 5 is a graph showing the relation between the kinetic energy of one shot detected by the apparatus of the present invention and the peak voltage of the detection output signal shown in FIG. 4.
Figure 6:
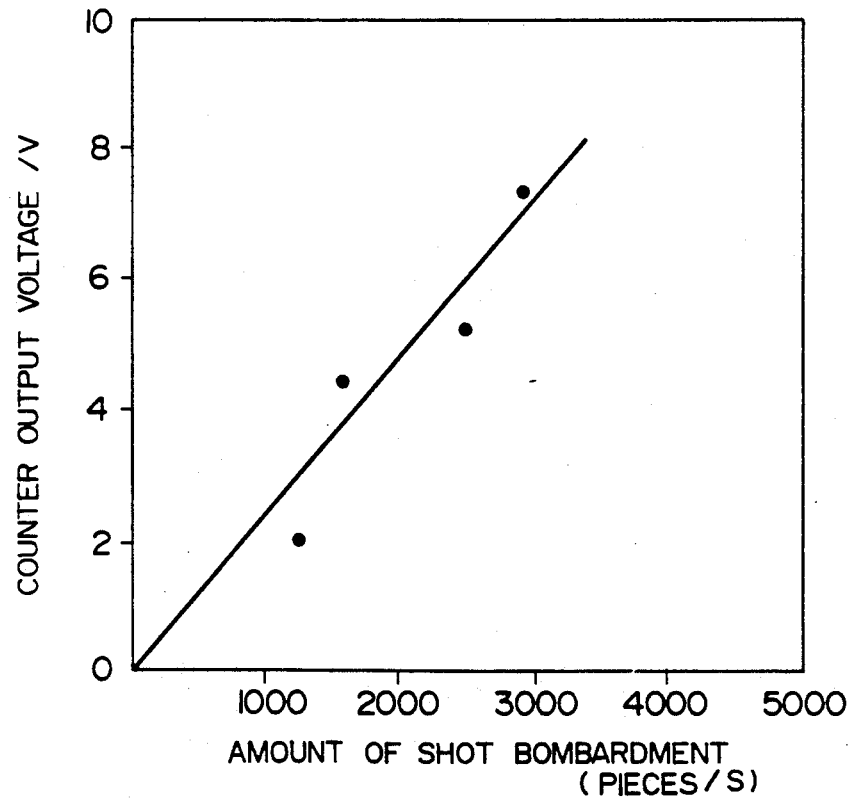
FIG. 6 is a graph showing the relation between the wave number of the detection output signal shown in FIG. 4 and the number of times of shot bombardment.

The apparatus 20 having the construction described above is mounted at its body portion 10 integral with the outer casing 3, at one corner in a shot projecting area of a shot blasting machine (not shown), and the relation between the kinetic energy of the shot and the peak voltage and also the relation between the number of times of shot bombardment and the counter output voltage are measured. FIGS. 5 and 6 show the results of measurement of the former and latter relations respectively obtained from an experimental study. It will be seen in FIG. 5 that the peak voltage is proportional to the kinetic energy of one shot, and it will also be seen in FIG. 6 that the counter output voltage is proportional to the number of times of shot bombardment.

Figure 7A:
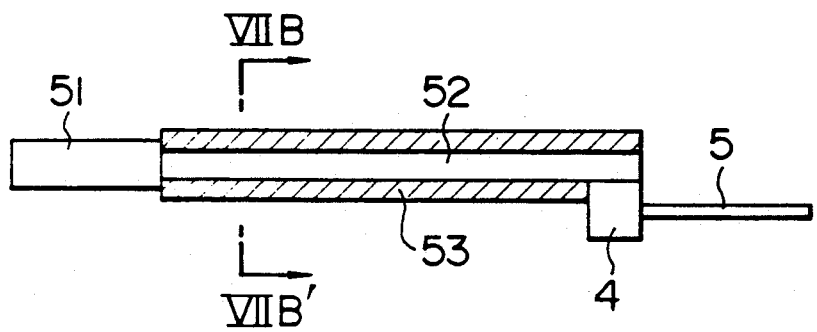
FIG. 7 is a schematic longitudinal sectional view showing the structure of another form of the shot bombardment and propagation member in another embodiment of the apparatus according to the present invention.
FIG. 7B is a cross sectional view taken along the line VIIB—VIIB, in FIG. 7A.
Figure 7B:
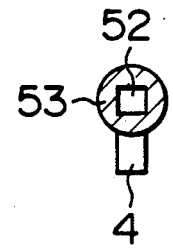

FIG. 7A shows another embodiment of the present invention in which a first part to be bombarded by a shot stream and a second part for propagating the elastic waves are separately provided. Referring to FIG. 7A, a member 52 for propagating the elastic waves in the form of a rod having a generally square sectional shape is connected at its one end to one end of a member 51 to be bombarded by a shot stream in the form of a rod having a generally square sectional shape. The transducer 4 is mounted on the other end of the member 52, and the output signal of the transducer 4 is supplied to the measuring circuit 30 by the cable 5. Shot stream is projected upward toward the member 51 from a lower part of FIG. 7A. More concretely, the member 51 is in the form of a rod which is made of, for example, sintered hard alloy and which has, for example, a length of 45 mm and a square sectional area of 15 mm × 15 mm. The member 52 is in the form of a rod which is made of, for example, steel and which has, for example, a length of 200 mm and a square sectional area of 10 mm × 10 mm. Further, the member 52 is covered with a rubber layer 53 as shown in FIG. 7B so as to protect the member 52 from wearing by the projection of the shot stream. This second embodiment also exhibits the effect similar to that exhibited by the first embodiment shown in FIG. 1A.

In the aforementioned embodiments, the AE sensor is used as the transducer 4 by way of example. However, it is apparent that any one of known transducers may be used provided that elastic waves generated at a very short time interval of, for exmaple, 5 ms can be continuously transduced into an electrical signal within a short period of time. Therefore, the transducer 4 may be a piezoelectric element such as, that made of quartz or lithium sulfate, an electrostrictive element such as, that made of barium titanate or lead zirconate titanate, or a high-frequency transducer element formed by evaporating a piezoelectric semiconductor such as, cadmium sulfide or zinc oxide on a cicular steel or copper sheet in a thickness corresponding to the halfwave length of the elastic wave.

The high-frequency electrical signal is subjected to the envelope detection in the aforementioned embodiments. However, without subjecting the high-frequency electrical signal to the envelope detection, the number of times of appearance of aforementioned single-waves or their peak values may be directly detected.

Figure 8:
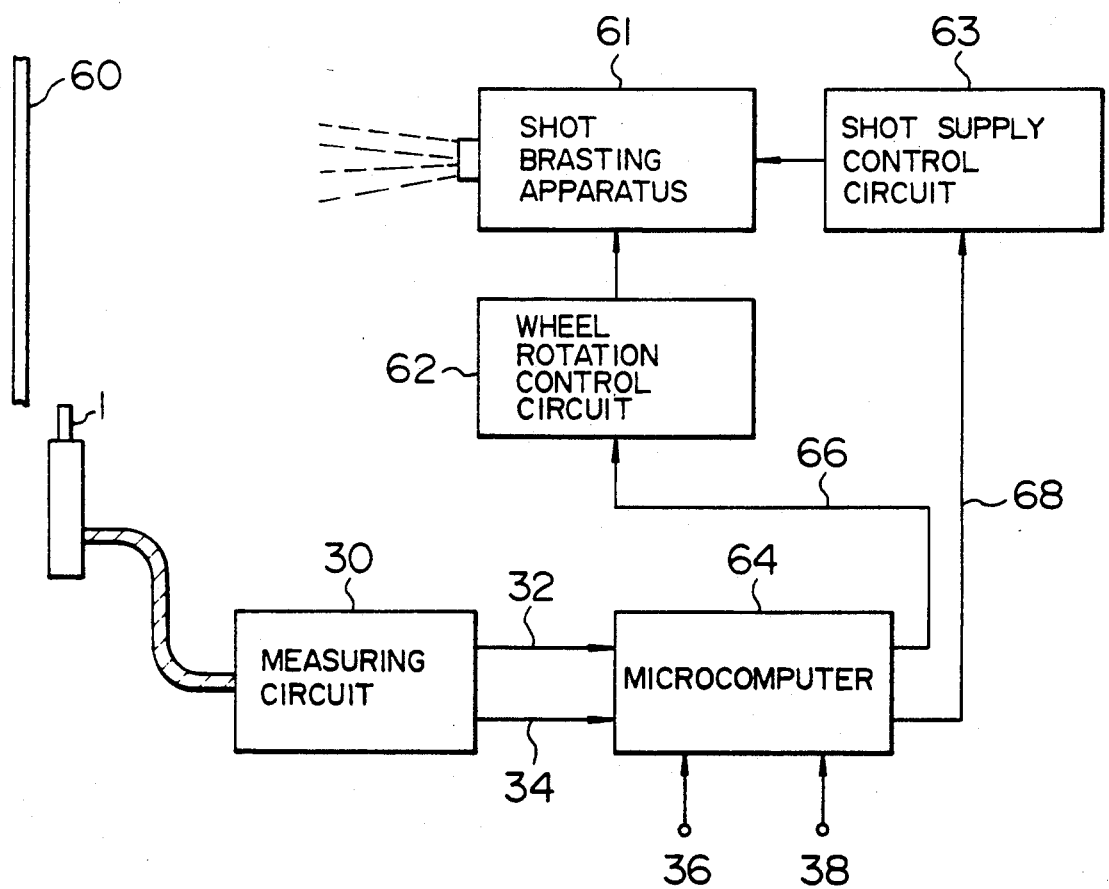
FIG. 8 is a block diagram showing the structure of one form of a system in which the output of the apparatus according to the present invention is used for controlling the intensity and density of shot blasting by a shot blasting apparatus.

FIG. 8 shows a system in which the output of the apparatus according to the present invention is used for controlling the intensity of shot blasting by a shot blasting machine. Referring to FIG. 8, the shot blasting machine 61 is, for example, of the type projecting a shot stream by rotation of a rotary wheel and includes therein a shot-blasting wheel rotation controller for controlling the intensity of shot blasting and a shot-stream supply controller for controlling the amount of the shot stream. The shot blasting machine 61 is supported by a suitable supporting and moving device (not shown) and is moved while projecting the shot stream toward and onto a steel work 60 to te treated at a predetermined distance from the steel work 60, so that the entire surface of the steel work 60 can be subjected to the shot treatment. In another mode, the steel work 60 may be moved while fixing the shot blasting machine 61 in position during the shot treatment, or both the shot blasting machine 61 and the steel work 60 may be moved during the shot treatment. The shot blasting machine 61 may be of the type of shot blasting by the pressure of an air blast.

The shot bombardment and propagation member 10 in the apparatus of the present invention is located adjacent to the steel work 60, and, when it receives the shot stream projected from the shot blasting machine 61 in the course of the shot treatment, the measuring circuit 30 generates output signals 32 and 34 indicative of the intensity of shot bombardment and the number of times of shot bombardment respectively. These signals 32 and 34 are applied to a microcomputer 64 to be compared with externally applied signals 36 and 38 indicating desired or target values of the intensity of shot bombardment and the number of times of shot bombardment respectively. When the microcomputer 64 decides that the difference between each of the measured values and the corresponding target value exceeds a predetermined setting, the microcomputer 64 computes control values corresponding to the errors and generates control signals 66 and 68 corresponding to the computed control values respectively. These control signals 66 and 68 are applied to a wheel rotation control circuit 62 and a shot supply control circuit 63 so as to control the rotation of the wheel of the shot blasting machine and the amount of the shot stream supplied from the shot blasting machine 61 respectively. Both the rotation of the shot blasting wheel and the amount of the supplied shot stream may be controlled by one of the signals 32 and 34 indicative of the intensity of shot bombardment and the number of times of shot bombardment respectively. A table showing the relation between control values and errors from individual target values has been experimentally prepared beforehand and is stored in the microcomputer 64, and the control values are computed on the basis of this table. Thus, the conditions for shot blasting can be most suitably controlled while executing the shot treatment.

We claim:

1. An apparatus for detecting at least one of an intensity and a density of shot blasting during shot treatment, comprising:
    shot bombardment and propagation means including a first part to be bombarded by a shot stream for generating elastic waves when bombarded by the shot stream and a second part for propagating said elastic waves therethrough;
    transducer means receiving said elastic waves from said shot bombardment and propagation means for transducing said elastic waves into a high-frequency electrical signal; and
    measuring means for detecting at least one of the number of times of shot bombardment and an intensity of shot bombardment on the basis of said high-frequency electrical signal;
    wherein said measuring means includes a counter circuit detecting the number of times of appearance of single-waves in said high-frequency electrical signal.

2. An apparatus according to any of claims 1, wherein the shot stream is projected with a shot blasting machine of the type of rotary wheel and including at least one of first means for controlling the rotation of the shot blasting wheel and second means for controlling the amount of the supplied shot stream, and the output signal of said counter circuit is used to control at least one of said first and second means.

3. An apparatus for detecting at least one of an intensity and a density of shot blasting during shot treatment, comprising:
    shot bombardment and propagation means including a first part to be bombarded by a shot stream for generating elastic waves when bombarded by the shot stream and a second part for propagating said elastic waves therethrough;
    transducer means receiving said elastic waves from said shot bombardment and propagation means for transducing said elastic waves into a high-frequency electrical signal; and
    measuring means for detecting at least one of the number of times of shot bombardment and an intensity of shot bombardment on the basis of said high-frequency electrical signal;
    wherein said measuring means includes an envelope detection circuit subjecting said high-frequency electrical signal to envelope detection, and a counter circuit detecting the number of times of generation of output signals from said envelope detection circuit.

4. An apparatus according to claim 3, wherein the shot stream is projected with a shot blasting machine of the type of air pressure and including at least one of first means for controlling the rotation of the shot blasting impeller and second means for controlling the amount of the supplied shot stream, and the output signal of said counter circuit is used to control at least one of said first and second means.

5. An apparatus for detecting at least one of an intensity and a density of shot blasting during shot treatment, comprising:
    shot bombardment and propagation means including a first part to be bombarded by a shot stream for generating elastic waves when bombarded by the shot stream and a second part for propagating said elastic waves therethrough;
    transducer means receiving said elastic waves from said shot bombardment and propagation means for transducing said elastic waves into a high-frequency electrical signal; and
    measuring means for detecting at least one of the number of times of shot bombardment and an intensity of shot bombardment on the basis of said high-frequency electrical signal;
    wherein said measuring means includes a peak measuring circuit detecting the peak values of the single-waves included in said high-frequency electrical signal.

6. An apparatus according to claim 5, wherein the shot stream is projected with a shot blasting machine of the type of rotary wheel and including at least oen of first means for controlling the rotation of the shot blasting wheel and second means for controlling the amount of the supplied shot stream, and the output signal of said peak measuring circuit is used to control at least one of said first and second means.

7. An apparatus for detecting at least oen of an intensity and a density of shot blasting during shot treatment, comprising:
    shot bombardment and propagation means including a first part to be bombarded by a shot stream for generating elastic waves when bombarded by the shot stream and a second part for propagating said elastic waves therethrough;
    transducer means receiving said elastic waves from said shot bombardment and propagation means for transducing said elastic waves into a high-frequency electrical signal; and
    measuring means for detecting at least one of the number of times of shot bombardment and an intensity of shot bombardment on the basis of said high-frequency electrical signal;
    wherein said measuring means includes an envelope detection circuit subjecting said high-frequency electrical signal to envelope detection, and a peak measuring circuit detecting the peak values in an output signal generated from said envelope detection circuit.

8. An apparatus according to claim 7, wherein the shot stream is projected with a shot blasting machine of the type of air pressure and including at least one of first means for controlling the rotation of the shot blasting impeller and second means for controlling the amount of the supplied shot stream, and the output signal of said peak measuring circuit is used to control at least one of said first and second means.

9. An apparatus according to any of claims 1-7, wherein the shot stream is projected with a shot blasting machine of the type of rotary wheel.

10. An apparatus according to any of claims 1-7, wherein the shot stream is projected with a shot blasting machine of the type of air pressure.

11. An apparatus according to any of claims 1-7, wherein said shot bombardment and propagation means includes a member of a wear resistant material bombarded by the shot stream, an outer casing, and a vibration isolating member preventing said member from vibration of said outer casing.

12. An apparatus according to any of claims 1-7, wherein said shot bombardment and propagation means includes a member of a wear resistant material bombarded by the shot stream, a rod-shaped wave propagating member connected at one end to said shot bombarded member, and a cover protecting said wave propagating member from wearing by the projection of the shot stream, and said transducer means is connected to the other end of said wave propagating member.

13. An apparatus according to any of claims 1-7, wherein said transducer means is a high-frequency transducer element including one of an AE sensor, a piezoelectric element and an electrostrictive element.

14. An apparatus for detecting at least one of an intensity and a density of shot blasting during shot treatment, comprising:

shot bombardment and propagation means including a first part to be bombarded by a shot stream for generating elastic waves when bombarded by the shot stream and a second part for propagating said elastic waves therethrough;

transducer means receiving said elastic waves from said shot bombardment and propagation means for transducing said elastic waves into a high-frequency electrical signal; and measuring means including a counter circuit for detecting the number of times of appearnace of single-waves in said high-frequency electrical signal, and a peak measuring circuit for detecting peak values of said single-waves.

15. An apparatus for detecting at least one of an intensity and a density of shot blasting during shot treatment, comprising:

shot bombardment and propagation means including a first part to be bombarded by a shot stream for generating elastic waves when bombarded by the shot stream and a second part for propagating said elastic waves therethrough;

transducer means receiving said elastic waves from said shot bombardment and propagation means for transducing said elastic waves into a high-frequency electrical signal; and measuring means including an envelope detection circuit subjecting said high-frequency electrical signal to envelope detection, a counter circuit detecting the number of times of appearance of output signals from said envelope detection circuit, and a peak measuring circuit detecting peak values of said output waves.

* * * * *